US007504554B2

(12) United States Patent
Liu et al.

(10) Patent No.: US 7,504,554 B2
(45) Date of Patent: Mar. 17, 2009

(54) ANIMAL MODEL FOR IDENTIFYING AGENTS THAT INHIBIT OR ENHANCE CTLA4 SIGNALING

(75) Inventors: Yang Liu, Columbus, OH (US); Pan Zheng, Columbus, OH (US); Ping Lu, Columbus, OH (US); Bedrich Mosinger, Columbus, OH (US); Ken May, Kettering, OH (US)

(73) Assignee: The Ohio State University Research Foundation, Columbus, OH (US)

( * ) Notice: Subject to any disclaimer, the term of this patent is extended or adjusted under 35 U.S.C. 154(b) by 95 days.

(21) Appl. No.: 11/620,935

(22) Filed: Jan. 8, 2007

(65) Prior Publication Data

US 2007/0283452 A1 Dec. 6, 2007

Related U.S. Application Data

(60) Continuation of application No. 11/052,559, filed on Feb. 7, 2005, now Pat. No. 7,161,058, which is a division of application No. 09/957,688, filed on Sep. 20, 2001, now Pat. No. 6,875,904.

(60) Provisional application No. 60/234,089, filed on Sep. 20, 2000.

(51) Int. Cl.
*G01N 33/00* (2006.01)
(52) U.S. Cl. .................. 800/3; 800/13; 800/18; 800/21; 800/24
(58) Field of Classification Search .................. None
See application file for complete search history.

(56) References Cited

U.S. PATENT DOCUMENTS

| 5,434,131 | A | * | 7/1995 | Linsley et al. ............ 514/2 |
| 5,855,887 | A | | 1/1999 | Allison et al. |
| 6,051,227 | A | | 4/2000 | Allison et al. |
| 6,875,904 | B2 | * | 4/2005 | Liu et al. ............. 800/18 |
| 7,161,058 | B2 | | 1/2007 | Liu et al. |

FOREIGN PATENT DOCUMENTS

WO 96/34888 A1 11/1996
WO 97/47732 A2 12/1997

OTHER PUBLICATIONS

Croxford et al. Eur J Immunol 1998;28:3904-16.*
Boucher, "Status of gene therapy for cystic fibrosis lung disease", J. Clin. Invest. (1999) vol. 103, No. 4, pp. 441-445.
Bowie et al., "Deciphering the Message in Protein Sequences: Tolerance to Amino Acid Substitutions", Science (1990) vol. 247, pp. 1306-1310.
Deonarain, "Ligand-targeted receptor-mediated vectors for gene deliver", Expert Opin. Ther. Pat. (1998) vol. 8, pp. 53-69.
Linder, "The Influence of Genetic Background on Spontaneous and Genetically Engineered Mouse Models of Complex Diseases", Lab Animal, (2001) vol. 30, No. 5, pp. 34-39.
Logan and Sharma, "Potential use of Genetically Modified Pigs as Organ Donors for Transplantation in Humans", Clin. Exp. Pharmacol. Physiol. (1999) vol. 26, pp. 1020-1025.
Robbins and Ghivizzani, "Viral Vectors for Gene Therapy", Pharmacol. Ther. (1998) vol. 80, No. 1, pp. 35-47.
Rudiger, "Characteristics of the amino acids as components of a peptide hormone sequence", Peptide Hormones (Jun. 1976) pp. 1-7.
Russell and Hirata, "Human gene targeting by viral vectors", Nat. Genet. (1998) vol. 18, pp. 325-330.
Verma and Somla, "Gene therapy—promises, problems and prospects", Nature (1997) vol. 389, pp. 239-242.
Waterhouse et al., "Lymphoproliferative Disorder with Early Lethality in Mice Deficient in Ctla-4", Science (1995) vol. 270, pp. 985-988.
Waterhouse et al., "Normal thymic selection, normal viability and decrease lymphoproliferation in T cell receptor-transgenic CTLA-4-deficient mice", European Journal of Immunology (1997) 27:1887-1892.
Office Action in U.S. Appl. No. 09/957,688, mailed Mar. 27, 2003.
Response to Office Action in U.S. Appl. No. 09/957,688, filed Jul. 28, 2003.
Office Action in U.S. Appl. No. 09/957,688, mailed Nov. 20, 2003.
Response to Office Action in U.S. Appl. No. 09/957,688, filed Feb. 19, 2004.
Notice of Non-Compliant in U.S. Appl. No. 09/957,688, mailed Mar. 4, 2004.
Response to Notice of Non-Compliant in U.S. Appl. No. 09/957,688, filed Mar. 12, 2004.
Office Action in U.S. Appl. No. 09/957,688, mailed May 26, 2004.
Response to Office Action in U.S. Appl. No. 09/957,688, filed Jul. 20, 2004.
Notice of Allowance for U.S. Appl. No. 09/957,688, mailed Oct. 28, 2004.
Preliminary Amendment in U.S. Appl. No. 11/052,559, filed Feb. 7, 2005.
Notice of Allowance for U.S. Appl. No. 11/052,559, mailed Sep. 5, 2006.

* cited by examiner

*Primary Examiner*—Q. Janice Li
(74) *Attorney, Agent, or Firm*—Calfee, Halter & Griswold LLP

(57) ABSTRACT

The present invention relates to a non-human transgenic animal, particularly a knock in mouse, whose genome comprises a heterologous, chimeric CTLA4 gene. The chimeric CTLA4 gene comprises exon 2 of the human CTLA4 gene, exon 1 and exon 4 of the non-human animal, and exon 3 of the CTLA4 gene of the non-human animal, or preferably, exon 3 of the human CTLA4 gene. The invention also relates to methods by which the transgenic mice are used to screen for monoclonal antibodies or other molecules that enhance immunity to tumors and infectious agents by interacting with the human CTLA4 receptor. The transgenic mice of the present invention are also useful for screening for monoclonal antibodies or other molecules that inhibit autoimmunity and transplant rejection.

4 Claims, 9 Drawing Sheets

```
M-CTLA4: 1  MACLGLRRYKAQLQLPSRTWPFVALLTLLFIPVFSEAIQVTQPSVVLASSHGVASFPCEY 60
            MACLG  R KAQL L  RTWP   L  LLFIPVF  A  V QP VVLASS G ASF CEY
H-CTLA4: 1  MACLGFQRHKAQLNLAARTWPCTLLFFLLFIPVFCKAMHVAQPAVVLASSRGIASFVCEY 60

. . . . . . . . . . . . . . . . . . . . . . .****************************
                                        exon 1

SPSHNTDEVRVTVLRQTNDQMTEVCATTFTEKNTVGFLDYPFCSGTFNESRVNLTIQGLR 120
                   EVRVTVLRQ  Q TEVCA T     N    FLD   C GT      VNLTIQGLR
            ASPGKATEVRVTVLRQADSQVTEVCAATYMTGNELTFLDDSICTGTSSGNQVNLTIQGLR 120

************************************************************
                                        exon 2

AVDTGLYLCKVELMYPPPYFVGMGNGTQIYVIDPEPCPDSDFLLWILVAVSLGLFFYSFL 180
            A DTGLY CKVELMYPPPY  G GNGTQIYVIDPEPCPDSDFLLWIL AVS GLFFYSFL
            AMDTGLYICKVELMYPPPYYLGIGNGTQIYVIDPEPCPDSDFLLWILAAVSSGLFFYSFL 180

********************************************---------------
                                        exon 3

VTAVSLSKMLKKRSPLTTGVYVKMPPTEPECEKQFQPYFIPIN 223
             TAVSLSKMLKKRSPLTTGVYVKMPPTEPECEKQFQPYFIPIN
            LTAVSLSKMLKKRSPLTTGVYVKMPPTEPECEKQFQPYFIPIN 223
            ------------------------------------------
                                        exon 4
```

Identities = 167/223 (74%), Positives = 189/223 (83%)

Key - shown under the amino acid sequence in the figure

Dotted line, putative leader sequence;

Line of asterisks, extracellular domain;

Dashed line, transmemberane region;

Plain line, the cytoplasmic tail

Fig. 1

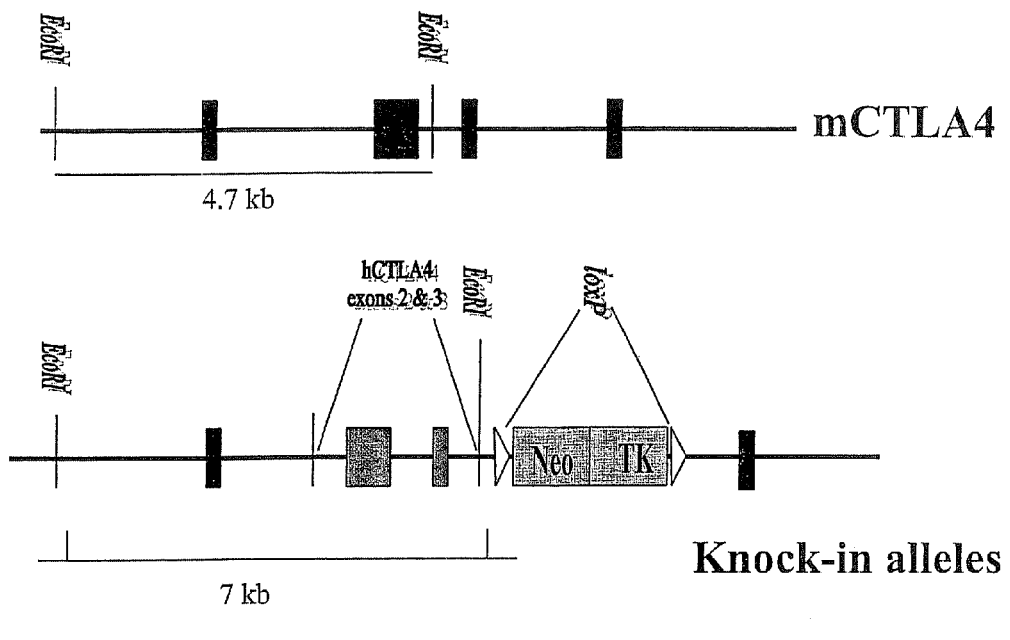
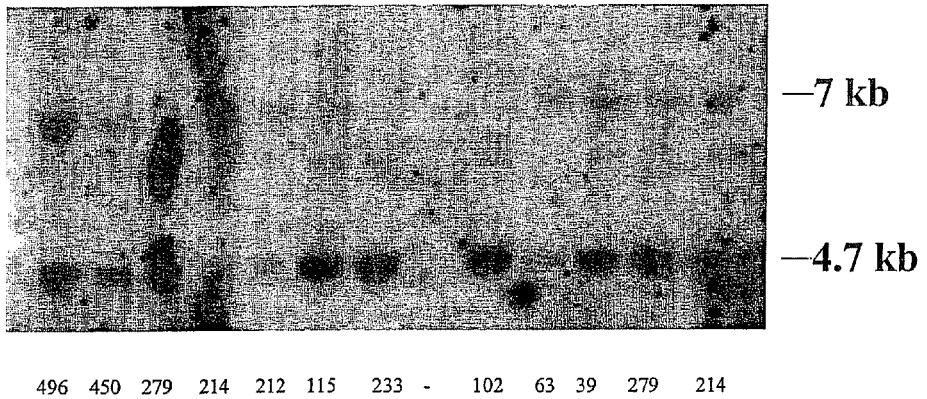
496 450 279 214 212 115 233 - 102 63 39 279 214
Fig. 4

ANIMAL MODEL FOR IDENTIFYING AGENTS THAT INHIBIT OR ENHANCE CTLA4 SIGNALING

This application is a continuation of application Ser. No. 11/052,559, filed Feb. 7, 2005, now U.S. Pat. No. 7,161,058, which is a division of application Ser. No. 09/957,688, filed Sep. 20, 2001, now U.S. Pat. No. 6,875,904, which claims the benefit of Provisional Application No. 60/234,089, filed Sep. 20, 2000, the disclosures of which are each hereby incorporated by reference herein.

BACKGROUND

Two types of signals are required for T cell activation and proliferation. The first gives specificity to the immune response and involves an interaction between the T-cell receptor/CD3 complex and an antigenic peptide presented by major histocompatibility complex (MHC) class I or class II proteins on the surface of an antigen-presenting cell (APC). The second, called a costimulatory signal, involves interaction between receptor-ligand pairs expressed on the surface of APCs and T cells. Antigenic stimulation in the absence of costimulation induces a state of unresponsiveness or anergy and eventual cell death by apoptosis in the responding T cells. Thus, antigenic stimulation in the presence of costimulation prevents anergy and cell death, thereby promoting cell survival.

A number of investigators have demonstrated that expression of the costimulatory ligands B7-1 and B7-2 on tumor cells can significantly increase immunogenicity of tumors, and induce tumor rejection by a T cell-dependent mechanism. (Baskar, S., Ostrand-Rosenberg, S., Nabavi, N., and Glimcher, L. (1993). Proc. Natl. Acad. Sci. USA. 90, 7015-7019; Chen, L., Ashe, S., Brady, W. A., Hellstrom, I., Hellstrom, K. E., Ledbetter, J. A., McGowan, P., and Linsley, P. S. (1992) Cell 71, 1093-102; Ramarathinam, L., Castle, M., Wu, Y., and Liu, Y. (1994). J Exp Med 179, 1205-14; Townsend, S. E., and Allison, J. P. (1993) Science 259, 368-370). CD28 and CTL4A are two T cell receptors that bind to the B7-1 and B7-2 ligands. CD28 is a transmembrane homodimer that is constitutively expressed on 90% of mammalian CD4+T cells. Engagement of CD28 by its ligands B7-1 or B7-2 on the surface of APCs initiates a signaling cascade culminating in cytokine production and expansion of specific T-cells. CTLA-4, a structural homologue of CD28, is a transmembrane protein that is expressed on activated T cells. The role of B7-CTLA4 interaction remains controversial. (Liu, Y. (1997). Immunol Today 18, 569-72).

Anti-CTLA4 Antibodies

Allison and colleagues have demonstrated that anti-mouse CTLA4 mAb induced rejection of tumors in vivo (Leach et al., 1996) Anti-CTLA4 mAb-treatment has also been shown to enhance immune response of mouse to bacteria. (Heinzel, F. P., and Maier, R. A., Jr. (1999). Infect Immun 67, 6454-60; Kirman, J., McCoy, K., Hook, S., Prout, M., Delahunt, B., Orme, I., Frank, A., and Le Gros, G. (1999). Infect Immun 67, 3786-92).

CTLA4 has also been shown to play an important role in autoimmune diseases. Numerous studies have linked the polymorphism of the CTLA4 gene in humans to a variety of autoimmune diseases, such as Graves' disease, Hashimoto's thyroiditis, myasthenia gravis with thymoma, and insulin-dependent diabetes mellitus. (Barbesino et al., 1998; Braun et al., 1998; Donner et al., 1997; Donner et al., 1997; Huang et al., 2000; Huang et al., 1998; Kotsa et al., 1997; Marron et al., 1997; Nistico et al., 1996; Tomer et al., 1997). In addition, treatment with anti-CTLA4 mAbs has been shown to exacerbate experimental autoimmune diseases such as diabetes (Luhder et al., 1998) and experimental autoimmune encephalomyelitis (animal model of human multiple sclerosis) (Karandikar et al., 1996) in animal models.

In most experimental models, the two most extensively used anti-murine CTLA4 mAbs enhanced T cell activation in vivo. Nevertheless, since different mAbs may react with different epitopes on the same region of a protein or alternatively, bind to the same epitope with different affinities, different mAbs against the same protein can have opposite effects. Thus, some monocloanal antibodies to the CTLA4 receptor may enhance T cell proliferation and activation; while other anti-CTLA4 monoclonal antibodies may inhibit T cell proliferation and activation. Accordingly, monoclonal antibodies and other agents which specifically or selectively interact with CTLA4 may be of therapeutic value in cancer, and infection, as well as autoimmune disease and transplantation.

A major impediment to the development or identification of mAbs or other agents that can be used to either activate or inactivate T cells via a CTLA4-mediated pathway is the lack of an appropriate assays for screening such agents. Conflicting results have demonstrated that an in vitro assay cannot serve as an accurate predictor of the functionality of antibodies to the B7 receptors in vivo. For example, anti-CD28 mAb have been shown to provide potent costimulatory activity for T cell activation in vitro (Jenkins et al., 1991), but have little effect on tumor growth in vivo (Leach et al., 1996). In contrast, investigators have found that administration of anti-CTLA4 mAb induces rejection of tumors and exacerbates autoimmune diseases in vivo (Leach et al.,) while anti-CTLA4 mAbs have been shown to either enhance or inhibit T cell activation in vitro (Krummel and Allison, 1995; Walunas et al., 1994) These results demonstrate that the functional effect of agents targeting receptors for B7 ligands, particularly the CTLA4 receptor, cannot be accurately tested in vitro. Accordingly, it is desirable to have additional tools for screening agents, particularly monoclonal antibodies, that either inhibit or enhance CTLA-4 signaling.

SUMMARY OF THE INVENTION

The present invention provides a new tool for testing the effect of agents which interact with the human CTLA4 receptor in vivo. The tool is a transgenic, non-human animal, preferably a knock in mouse, whose T cells express a CTLA4 protein that comprises the extracellular domain of the human CTLA4 protein. Incorporated into the genome of the transgenic animal is a transgene which comprises exon 1 and exon 4 of the CTLA4 gene of the animal and exon 2 of the human CTLA4 gene. Such transgene is referred to hereinafter as a "humanized CTLA4 transgene". The humanized CTLA4 transgene further comprises exon 3 of the CTLA4 gene of the animal or, preferably exon 3 of the human CTLA4 gene. Preferably, the transgenic animal is a knock in mouse in which the humanized CTLA4 transgene replaces the endogenous CTLA-4 locus through homologous recombination. Such animals are useful for testing the effects of agents which interact with the extracellular domain or transmembrane domain of the human CTLA4 receptor and alter CTLA4 signaling. Such animals are especially useful for identifying agents, particularly monoclonal antibodies, that may have a beneficial effect of transplant patients or patients with cancer, a pathognic infection, or an autoimmune disease.

The present invention also provides methods which employ the CTLA4 knock in mouse of the present invention for screening, identifying, and testing the in vivo effects of agents, particularly, monoclonal antibodies targeted at the human CTLA4 receptor, particularly the extracellular or transmembrane domain thereof. Such method will allow production of agents that can have therapeutic value for human cancer, chronic infection, and autoimmune diseases.

The present invention also relates to a DNA construct for preparing the CTLA4 knock in mouse of the present invention.

BRIEF DESCRIPTION OF THE FIGURES

FIG. 1. Comparison of the amino acid sequences of the proteins (H-CTLA4, SEQ ID NO:2) encoded by human CTLA4 gene, and the protein (M-CTLA4, SEQ ID NO:1) encoded by the murine CTLA4 gene. The amino acids shown between H-CTLA4 (SEQ ID NO:2) and M-CTLA4 (SEQ ID NO:1) are those amino acids common to and conserved between both the human and mouse sequences. Note 100% identity in amino acids of exon 4, which encodes the cytoplasmic domain of the two homologues.

FIG. 4. Southern blot for verification of the homologous recombination. A band of 7.0 kb indicates homologous recombination, while a 4.7 kb band indicate endogenous mouse CTLA4 alleles.

DETAILED DESCRIPTION OF THE INVENTION

Definitions

Figure 2A:
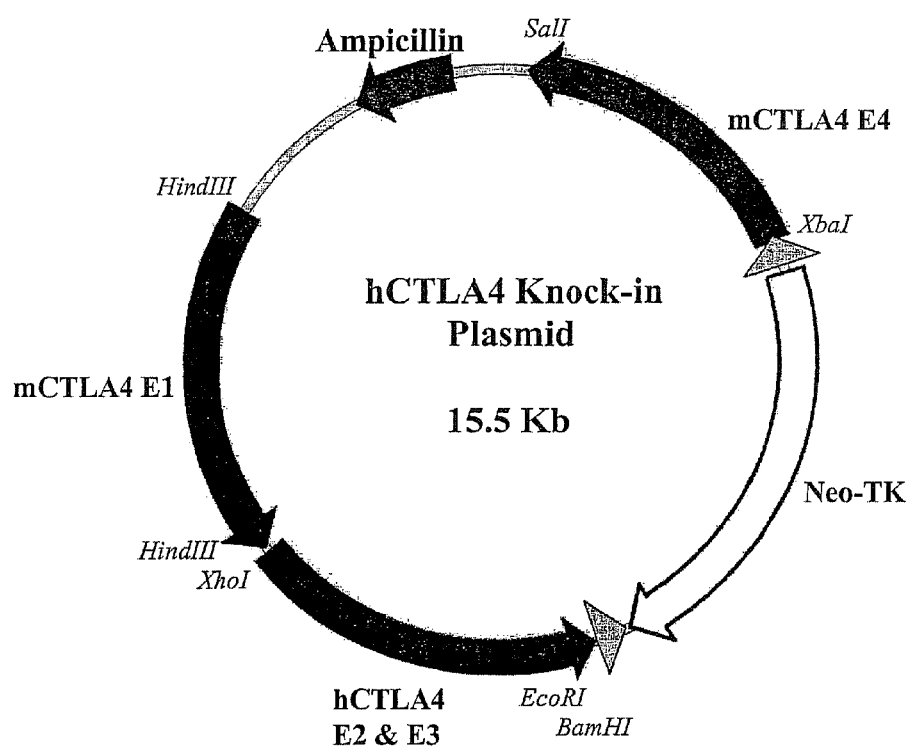
FIG. 2. Diagram of construct used for the production of human CTLA4 knock-in ES cells.
  a. Constructs for humanized CTLA4 knock-in mice. Note that part of intron 1, exon 2, intron 2, and exon 3 of the endogenous mouse CTLA4 gene are replaced by human CTLA4 sequence. The Neo-TK selection cassette is flanked by lox P sequence. The selection cassette is removed after Cre-mediated recombination to ensure controlled expression of the humanized CTLA4 transgene.
  b. Genomic structure of mouse (upper), human (lower) CTLA4 genes.
  c. Genomic structure of the humanized CTLA4-knock-in locus, and structure of the locus after the elimination of the Neo-TK cassette by the cre recombinase.

As used herein, the following terms and phrases shall have the meanings set forth below:

"Transgenic animal" is intended to include any non-human, vertebrate animal in which one or more of the cells of the animal contain heterologous nucleic acid encoding a humanized CTLA4 CTLA4 receptor. The heterologous nucleic acid is introduced into the animal by way of human intervention, such as by trangenic techniques well known in the art. Preferably, the heterologous nucleic acid is integrated within a chromosome in the cell. Preferably, integration into the chromosome is the result of homologous recombination between the endogenous CTLA4 locus and the transgene. In a highly preferred embodiment, the animal is a CTLA4 knock in mouse.

As used herein, the term "transgene" means a nucleic acid sequence encoding a humanized CTLA4 receptor. The transgene, which comprises exon 2 of the human CTLA4 protein, is heterologous, i.e., foreign, to the transgenic animal or cell into which it is introduced. Preferably the transgene includes introns that may be necessary for optimal expression of the transgene.

The term "transgenic gene construct" refers to a nucleic acid molecule, e.g., a vector, containing the subject gene, e.g., the humanized CTLA4 transgene, operably linked in a manner capable of expressing the gene in a host cell. The humanized CTLA4 gene construct can be introduced into a non-human animal cell by nucleic acid-mediated gene transfer. As used herein, the term "nucleic acid" refers to polynucleotides such as deoxyribonucleic acid (DNA), and, where appropriate, ribonucleic acid (RNA). As used herein the term also encompasses analogs of either RNA or DNA made from nucleotide analogs, and, as applicable to the embodiment being described, single-stranded (such as sense or antisense) and double-stranded polynucleotides.

The term "transcriptional regulatory sequence" refers to DNA sequences, such as initiation signals, enhancers, and promoters, which induce or control transcription of protein coding sequences with which they are operably linked. In preferred embodiments, transcription of a recombinant humanized CTLA4 transgene is under the control of a promoter sequence (or other transcriptional regulatory sequence) which controls the expression of the recombinant gene in a cell-type in which expression is intended.

The present invention provides a non-human, transgenic, vertebrate animal, whose genome comprises a humanized CLTA4 transgene. The humanized CTL4A transgene comprises exon 2 of the human CTLA4 gene, exon 1 and exon 4 of the transgenic animal, and exon 3 of the CTLA4 gene of the transgenic animal, or preferably exon 3 of the human CTLA4 gene. In a preferred embodiment the transgenic animal is a CTLA4 knock in mouse whose endogenous CTLA4 locus is replaced with the humanized CTLA4 transgenic by homologous recombination. The CTLA4 protein encoded by the humanized CTLA4 transgene is expressed on activated T cells The present invention also comprises a DNA construct for producing the transgenic animal.

The present invention also relates to methods which use the present transgenic animals, particularly the present transgenic mice, as a model to screen for mAbs or other molecules that interact with human CTLA4 protein and thereby either enhance immunity against tumor or chronic infection in vivo, or inhibit autoimmunity and transplant rejection in animal models.

1. Humanized CTLA4 Gene and Protein

Both murine and human CTLA4 genes consist of 4 exons [Dariavach, 1988; Harper, 1991). The sequence of the murine CTLA4 gene has the Genbank Accession Number AF142145. The sequence of human CTLA4 gene was published in Genomics, 60: 341-355, 1999 and has the Genbank Accession Number AF142144. Exon one, which encompasses nucleotide 1050 through nucleotide 1158 of the murine CTLA4 gene and nucleotide 1193 through nucleotide 1301 of the human CTLA4 gene encodes a signal peptide. Exon 2, which encompasses nucleotide 4302 through nucleotide 4649 of the murine CTLA4 gene and nucleotide 3829 through nucleotide 4176 of the human CTLA4 gene encodes the extracellular domain. Exon 3, which encompasses nucleotide 5098 through nucleotide 5207 of the murine CTLA4 gene and nucleotide 4621 through nucleotide 4730 of the human CTLA4 gene, encodes the transmembrane domain. Exon 4, which encompasses nucleotide 6488 through nucleotide 6592 of the murine CTLA4 gene and nucleotide 5951 through nucleotide 6055 of the human CTLA4 gene, encodes the cytoplasmic domain of the receptor.

The amino acid sequence encoded by exon one of the CTLA4 gene is not present in the mature CTLA 4 protein. The amino acid sequences of the murine CTLA4 protein, SEQ ID NO. 1, and the human CTLA4 protein, SEQ ID NO. 2, are shown in FIG. 1. As shown in FIG. 1, the murine and human CTLA4 proteins have 100% identity in their cytoplasmic domain. Thus, it is expected that T cells which express a chimeric CTLA4 receptor comprising the extracellular domain of human CTLA4 and the cytoplasmic domain of murine CTLA4 should transduce signals initiated by anti-human CTLA4 mAb or other agents targeted at the human CTLA4 receptor, particularly the extracellular and/or transmembrane domain thereof.

2. Transgenic Animals

The "non-human animals" of the invention comprise any non-human animal having an immune system capable of producing a cell-mediated immune response. Such non-human animals include vertebrates such as rodents, non-human primates, sheep, dog, cow, amphibians, reptiles, etc. Preferred non-human animals are selected from the rodent family including rat and mouse, most preferably a CTLA4 knock in mouse.

The transgenic non-human animals of the invention are produced by introducing a humanized CTLA4 transgene into the germline of the non-human animal. Embryonal stem cell (ES) are the primary type of target cell for introduction of the humanized CTLA4 transgene into the non-human animal in order to achieve homologous recombination. ES cells are obtained from pre-implantation embryos cultured in vitro and fused with embryos (Evans, M. J., et al. (1981) Nature 292, 154-156; Bradley, M. O., et al. (1984) Nature 309, 255-258; Gossler, et al. (1986) Proc. Natl. Acad. Sci U.S.A. 83, 9065-9069; and Robertson, et al. (1986) Nature 322, 445-448). Transgenes can be efficiently introduced into the ES cells by DNA transfection or by retrovirus-mediated transduction. Such transformed ES cells can thereafter be combined with blastocysts from a non-human animal. The ES cells thereafter colonize the embryo and contribute to the germ line of the resulting chimeric animal. For review see Jaenisch, R. (1988) Science 240, 1468-1474. The transfected embryonal cells may be incubated in vitro for varying amounts of time, or reimplanted into the surrogate host, or both.

Transgenic offspring of the surrogate host may be screened for the presence and/or expression of the transgene by any suitable method. Screening is often accomplished by Southern blot or Northern blot analysis, using a probe that is complementary to at least a portion of the transgene. Western blot analysis using an antibody against the protein encoded by the transgene may be employed as an alternative or additional method for screening for the presence of the transgene product. Typically, n transgenic mice, DNA is prepared from tail tissue and analyzed by Southern analysis or PCR for the transgene. Alternatively, the tissues or cells believed to express the transgene at the highest levels are tested for the presence and expression of the transgene using Southern analysis or PCR, although any tissues or cell types may be used for this analysis. Progeny of the transgenic animals may be obtained by mating the transgenic animal with a suitable partner, or by in vitro fertilization of eggs and/or sperm obtained from the transgenic animal.

Methods of producing transgenic mice via homologous recombination between the endogenous gene and a transgene construct are described by Hanks, M et al (Science 269: 679-682, 1995), which is specifically incorporated herein by reference. Detailed methods for generating non-human transgenic animal are described herein and in the section entitled "Examples" below.

DNA Construct

Humanized CTLA4 receptors can be can be expressed from a chimera locus comprising mouse exon 1, human exon 2, mouse or human exon 3 and human exon 4. One embodiment of the construct comprises exon 1 and exon 4 of the murine CTLA4 gene, exon 3 of the human CTLA4 gene, and exon 3 of the human or murine CTLA4 gene. Preferably, the construct comprises other regulatory sequences such as for example a promoter. If additional flanking sequence are useful in optimizing expression, such sequences can be cloned using the existing sequences as probes. Additional sequences necessary for maximizing processing of the transgene can be derived from either cDNA or genomic sequences.

Figure 2B:
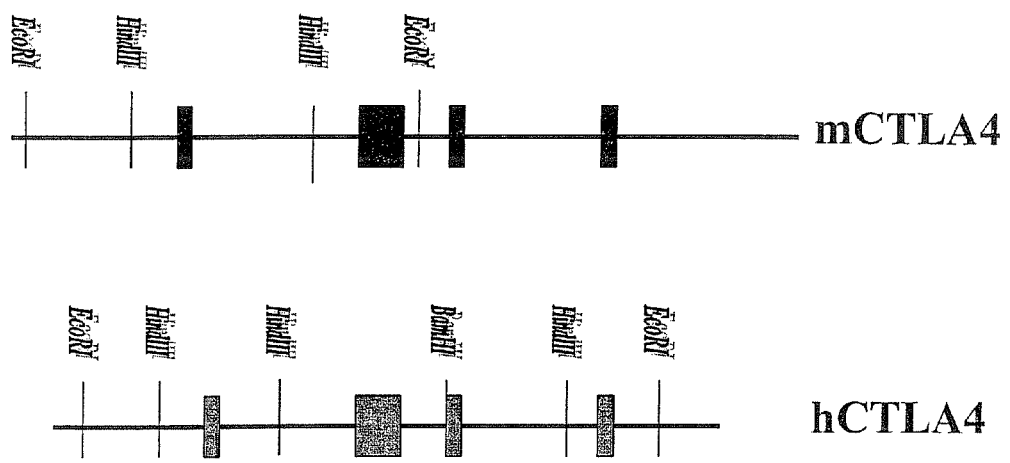

The construct or expression system can be part of a larger plasmid. The construct or expression system can be located between convenient restriction sites on the plasmid so that it can be easily isolated from the remaining plasmid sequences for incorporation into the desired animal. Partial restriction maps of the human CTLA4 gene and the murine CTLA4 gene are depicted in FIG. 2b.

Various methods employed in the preparation of the plasmids and transformation of host organisms are known in the art. For other suitable expression systems for both prokaryotic and eukaryotic cells, as well as general recombinant procedures, see Molecular Cloning A Laboratory Manual, 2nd Ed., ed. by Sambrook, Fritsch and Maniatis (Cold Spring Harbor Laboratory Press: 1989) Chapters 16 and 17.

The transgenic animals of the present invention are useful for testing agents that interact with the extracellular domain of human CTLA4 receptor, and that either enhance or inhibit CTLA4 signaling in vivo.

Anti-Human CTLA4 Receptor Agents

The agents are molecules that specifically bind to the extracellular domain, the transmembrane domain, or both domains of the human CTLA-4 receptor. The agents will be substantially unreactive with related molecules to CTLA-4, such as CD28 and other members of the immunoglobulin superfamily. Candidate agents are screened for their ability to meet this criteria. Assays to determine affinity and specificity of binding are known in the art, including competitive and noncompetitive assays. Assays of interest include ELISA, RIA, flow cytometry, etc. Binding assays may use purified or semi-purified CTLA-4 protein, or alternatively may use T cells that express CTLA-4, e.g. cells transfected with an expression construct for CTLA-4; T cells that have been stimulated through cross-linking of CD3 and CD28. The agents are peptides, small organic molecules, peptidomimetics, antibodies, or the like. Antibodies are preferred agents. Antibodies may be polyclonal or monoclonal; intact or truncated, e.g. F(ab').sub.2, Fab, Fv; xenogeneic, allogeneic, syngeneic, or modified forms thereof, e.g. humanized, chimeric, etc.

Suitable antibodies for use as blocking agents are obtained by immunizing a host animal with peptides comprising all or a portion of CTLA-4 protein. Suitable host animals include mouse, rat, sheep, goat, hamster, rabbit, etc. The origin of the protein immunogen may be mouse, human, rat, monkey etc. The host animal will generally be a different species than the immunogen, e.g. mouse CTLA-4 used to immunize hamsters, human CTLA-4 to immunize mice, etc. The human and mouse CTLA-4 contain highly conserved stretches in the extracellular domain (Harper et aL (1991) J. Immunol. 147: 1037-1044). Peptides derived from such highly conserved regions may be used as immunogens to generate cross-specific antibodies.

The immunogen may comprise the complete protein, or fragments and derivatives thereof. Preferred immunogens comprise all or a part of the extracellular domain of human CTLA-4, where these residues contain the post-translation modifications, such as glycosylation, found on the native CTLA-4. Immunogens comprising the extracellular domain are produced in a variety of ways known in the art, e.g. expression of cloned genes using conventional recombinant methods, isolation from T cells.

Monoclonal antibodies are produced by conventional techniques. Generally, the spleen and/or lymph nodes of an immunized host animal provide a source of plasma cells. The plasma cells are immortalized by fusion with myeloma cells to produce hybridoma cells. Culture supernatant from individual hybridomas is screened using standard techniques to identify those producing antibodies with the desired specificity. Suitable animals for production of monoclonal antibodies to the human protein include mouse, rat, hamster, etc. To raise antibodies against the mouse protein, the animal will generally be a hamster, guinea pig, rabbit, etc. The antibody may be purified from the hybridoma cell supernatants or ascites fluid by conventional techniques, e.g. affinity chromatography using CTLA-4 bound to an insoluble support, protein A sepharose, etc.

The antibody may be produced as a single chain, instead of the normal multimeric structure. Single chain antibodies are described in Jost et al. (1994) J.B.C. 269:26267-73, and others. DNA sequences encoding the variable region of the heavy chain and the variable region of the light chain are ligated to a spacer encoding at least about 4 amino acids of small neutral amino acids, including glycine and/or serine. The protein encoded by this fusion allows assembly of a functional variable region that retains the specificity and affinity of the original antibody.

Most of the diseases the anti-CTLA4 mAbs are designed to treat have a long clinical course, and may therefore require long-term treatment. In order to avoid potential immunogenicity of the mAbs in human, the mAbs that have the desired function are preferably humanized. "Humanized" forms of non-human (e.g., murine) antibodies are chimeric antibodies which contain minimal sequence derived from non-human immunoglobulin. For the most part, humanized antibodies are human immunoglobulins (recipient antibody) in which hypervariable region residues of the recipient are replaced by hypervariable region residues from a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues which are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. For further details, see Jones et al., Nature 321: 522-525 (1986); Reichmann et al., Nature 332: 323-329 (1988); and Presta, Curr. Op. Struct. Biol. 2: 593-596 (1992)

Alternatively, transgenic mice with human IgV and IgC genes may be used to produce human mAb specific for human CD24. These mice are available from Abgenix, and the art has been described fully (Nature Genetics, 1997, 15: 146).

Methods of Assessing the Effects of Anti-Human CTLA4 Monoclonal Antibodies

The animals of the present invention can be used to assess the in vivo effect of agents, particularly anti-human CTLA4 monoclonol antibodies, on tumors, infections, autoimmune diseases, and transplanted tissue that are present in these transgenic animals.

For example, tumor cells can be introduced into the transgenic animal and the effect of agents, which are then administered to the animal, on the growth of the tumor cells evaluated. Similarly, foreign tissue or infectious agents may be introduced into the transgenic animals and the effect of the agent on rejection of the tissue or prevention of diseases caused by the infectious agents determined. The transgenic animals of the present invention can be bred with animals that have a model autoimmune disease and the effect of the agent, particularly anti-human CTLA4 antibodies, on the disease monitored.

The screening of anti-CTLA4 mAb using the transgenic CTLA4-H(+/+) mice with tumors serves two purposes, one is to select the most effective mAbs, and the other is to determine the type of cancer whose growth may be inhibited by the mAb. Since anti-CTLA4 mAbs have the potential to activate both CTL and NK cells which have opposite selectivity for tumor cells with regard to their cell surface expression of MHC class I HLA-A, B, and C in human, the type of cancers to be treated will be prescreened for their expression of HLA-A, B, or C on the cell surface. The most convenient method is immunohistochemical staining of the cancer cells according to established procedures in the art. A commercially available mAb W6/32, which binds all known alleles of human HLA-A, B and C will be most suitable for the purpose. We have designed two indicator screening systems in the mouse to identify the mAb that are selective for activation of NK or CTL-mediated tumor rejection. The cancers that are devoid of HLA-A, B, and C, will be treated with mAb that are more efficient in inducing NK cell activation, while those having significant levels of HLA-A, B or C, will be treated with mAbs that are most suitable for activation of CTL. In many cases, cancer cells are heterogeneous with regards to their cell surface HLA expression. In these cases, a mixture of the two types of mAbs will be used. The anti-CTLA4 mAbs may be used in combination with other therapy, including other immunotherapy known in the art and chemotherapy if it does not interfere with the normal function of T cells and NK cells.

The transgenic animals prepared in accordance with the present invention may also be used to identify anti-human CTLA4 antibodies that enhance CTL mediated immunity against infectious agents. The anti-CTLA4 mAb which enhance CTL-mediated immunity against infectious agents can be used therapeutically in a wide range viral infections or other infectious intracellular parasites. Patients that have chronic viral infection will be treated with an effective dose of anti-human CTLA4 mAbs on a weekly basis. The effect of the antibodies will be monitored by both the reduction of viral titers, and in the elimination of viral mutants that were known to be resistant to recognition of the existing CTL in the patients. The anti-CTLA4 mAbs may be used in combination with other therapy, including other immunotherapy known in the art and chemotherapy if it does not interfere with the normal function of T cells and NK cells. For example, in the HIV-infected individuals, the anti-CTLA4 mAb can be combined with either AZT or with HAARD therapy.

In contrast to therapy for cancer and infection, the anti-CTLA4-mAb used for the treatment of autoimmune diseases must inhibit the function of the pathogenic T cells. Those antibodies that meet the criteria will be applied to patients of a number of autoimmune disease where T cells are responsible for the pathogenesis. The antibodies can be applied to multiple sclerosis patients, or patients with insulin-dependent diabetes.

The present invention is further illustrated by the following examples which should not be construed as limiting in any way. The contents of all cited references (including literature references, issued patents, published patent applications, and co-pending patent applications) cited throughout this application are hereby expressly incorporated by reference.

EXAMPLES

Example 1

Production of a Humanized CTLA4 Transgene Construct

Figure 2C:
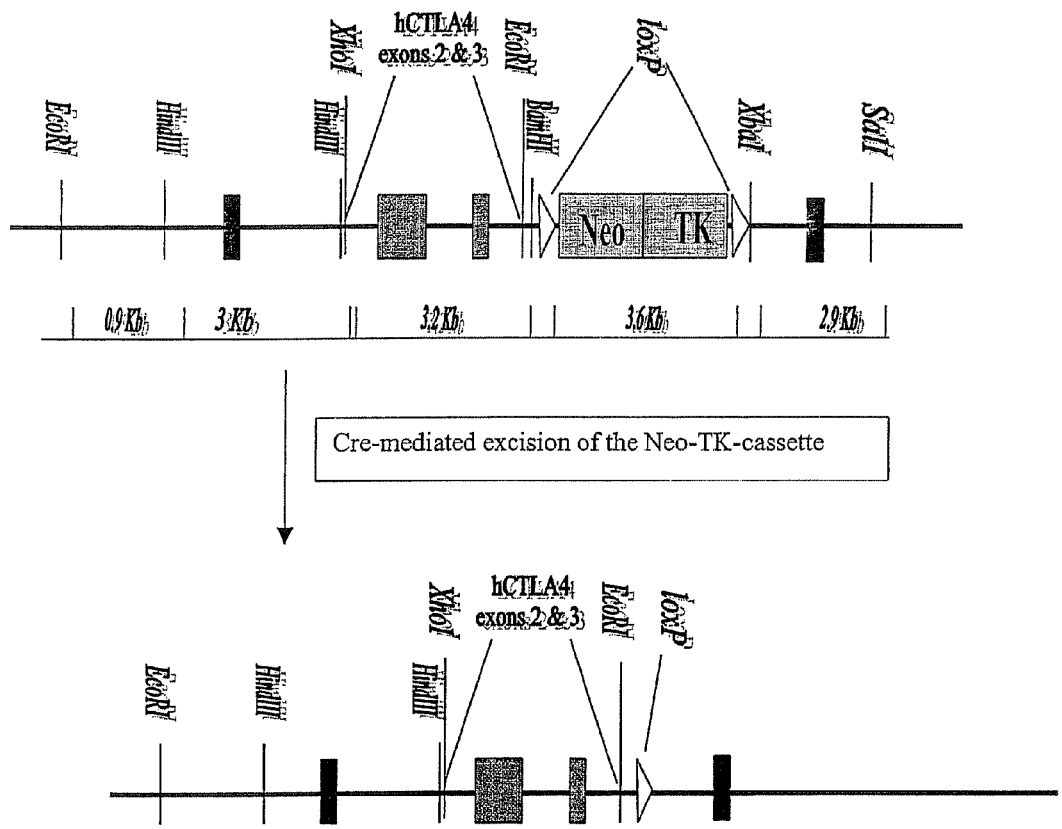

A DNA construct, containing the 5' promoter region, exon 1, intron 3, exon 4, and some additional 3' sequence from a murine CTLA4 gene clone purchased from the Genomic System Inc. (St. Louis, Mo.), and exon 2, intron 2, and exon 3 from a human CTLA4 gene isolated from a lamda phage clone (Dariavach et al., 1988; Harper et al., 1991), was prepared using standard recombinant techniques. Such constructs are illustrated in FIG. 2a. The physical map of the human and CTLA4 genes are presented in FIG. 2b. Two forms of the resulting "humanized" CTLA4 mouse transgene, is shown in FIG. 2c, One of the constructs comprises a Neo-TK cassette flanked by loxP sequence (floxed), while the other comprises an uninterrupted humanized CTLA4 mouse transgene.

More specifically, DNA containing a 14 Kb fragment of human CTLA4 gene was prepared from a lamda phage clone and digested with the restriction enzyme Hind III. A 3.2 kb Hind III fragment containing part of intron 1, exon 2, intron 2 and exon 3 of the human CTLA4 gene was purified and inserted into a Hind III-digested pBluescript plasmid. Plasmid DNA with the correct orientation insert was linearized by Xho I digestion, partially digested with BamH I, and a 3.2 Kb BamH1 fragment isolated for further cloning.

The P1 clone containing a 100 Kb murine CTLA4 gene was purchased from Genomic Systems Inc. (St. Louis, Mo.). A 3.8 kb DNA fragment containing 5' promoter region, exon 1 and part of intron 1 of the murine CTLA4 gene was cloned by PCR methods. The two primers used are CTGAAGCTTCAGTTTCAAGTTGAG, SEQ ID NO. 3 and TTGGATGGTGAGGTTCACTC, SEQ ID NO.4, which correspond respectively to sequence starting at base 734 of 5' promoter region and base 4524 of exon 2 region (Based on the numbering of the data from Genebank accession number: AF142145).

A 2.9 Kb DNA fragment containing part of intron 3, exon 4 and part of 3' sequence of the murine CTLA4 gene was cloned from the P1 clone by PCR method. The primers used are ATCCTCTAGAAGCTTCAAAGCAGGTTATCA, SEQ ID NO. 5, and TCTAGTCGACCACAGAGAGTCAAGGCCCTG, SEQ ID NO. 6, which correspond respectively to 6160 base through base 6181 of intron 3 regions and to 8617 base through base 8588 of 3' region.

The PCR product digested by Xba I and Sal I was inserted into pFlox clone containing mouse CTLA4 exon 1 and human CTLA4 exons 2 and 3. The final construct is illustrated in FIG. 2a.

Example 2

Figure 3:
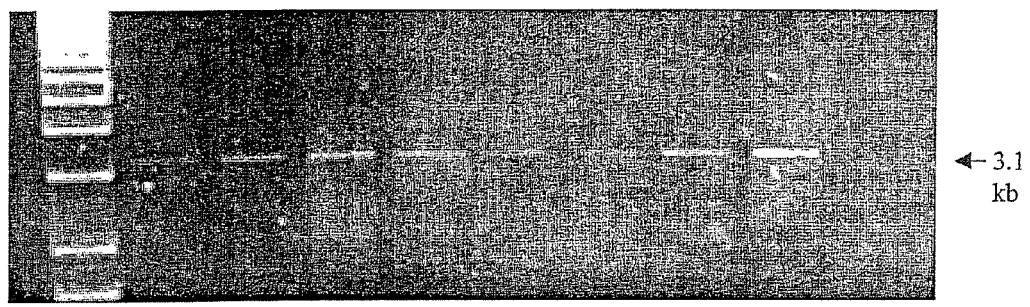
FIG. 3. PCR screening of the ES cells for homologous recombination. A PCR product of 3.1 kb indicates homologous recombination. No product can be amplified from mouse CTLA4 alleles.

Production by Homologous Recombination of a Transgenic (Knock-in) Mouse Whose T Cells Express a "Humanized" CTLA4 Protein A. Preparation of Embryonic Stem Cells with a Disrupted Humanized CTLA4 Transgene We transfected an embryonic stem cell line R1 with the DNA construct of Example 1 by electroporation. After selection with neomycin (G418), the DNA was isolated from drug-resistant clones and screened for homologous recombination by PCR. The forward primer used corresponds to a 5' sequence of the mouse CTLA4 gene outside the construct and the reverse primer is based on a unique sequence found in the human second exon. A homologous event yields a band of 3.1 Kb. As shown in FIG. 3, we identified 8 clones from 153 screened.

More specifically, the plasmid prepared as described in Example 1 was linearized by Sal I digestion. Approximately $2 \times 10^7$ ES cells were suspended in culture media (DMEM) without serum and electroporated in the presence of 30 μg of the humanized CTLA 4 transgene construct. The cells with the construct were placed, in volume of 0.8 ml, in an electroporation chamber with 4 mm distance between the electrodes. An electric discharge of 240V and from capacitance of 500 F was used to deliver one electric pulse to the ES cells using a BioRad Gene Pulser. The electroporated ES cells were then resuspended in growth media and plated onto eight 100 mm plastic dishes containing mitomycinized fibroblasts. After 24 hr the media was replaced with the selection media containing 150 μg/ml active G418 and changed daily.

ES colonies resulting after 10 days of selection were trypsinized, and individual cells picked using Eppendorf-type yellow tips and transferred individually to 24-well culture plates with mitomycinized fibroblasts. After a week of culture one half of the individual ES clones was used to prepare DNA for analysis and the second half was frozen in the presence of 10% DMSO and stored at −80° C. for further use.

To verify the homologous recombination, DNA isolated from the ES cells was digested with restriction endonuclease, transferred into nylon membrane, and hybridized with a $^{32}$P-labeled probe corresponding to a sequence at the 5' end of the mouse CTLA4 gene. Homologous recombination yielded a band of 7.0 kb, while the endogenous murine CTLA4 gene yielded a band of 4.7 kb. Data in FIG. 4 indicate that all clones that scored positive in PCR have homologous recombination.

DNA was extracted from ES clones by lysis in a buffer containing SDS and proteinase K, incubation at 60° C. for 24 hr, followed by phenol/chloroform extraction, and ethanol precipitation. 50 to 100 ng of DNA were used for analysis by PCR. Reactions were performed in 50 μl of PCR buffer with 1 U of Taq polymerase, 150 μM dNTPs and 0.4 μM of each primer. The reaction consisted of 36 cycles with 20 second (s) at 94° C., 40 s at 58° C., and 3 min 30s at 72° C. on a thermal cycler (PE Biosystems). The first priming oligonucleotide P1 gF of sequence CCAAGACTCCACGTCTCCAG, SEQ ID NO. 7 corresponds to the region upstream of the 1$^{st}$ exon of the mouse CTLA-4 gene, that is outside of the region used in the transgene construct. The second priming oligonucleotide Hu4.2R2 of sequence CCTCTGAGCATCCTTAGCAC, SEQ ID NO. 8 corresponds to the 2$^{nd}$ exon of the human CTLA-4 gene. These two primers give rise to a PCR product of 3300 base pairs (bp) only when the human exon is inserted into the mouse CTLA-4 gene by homologous recombination. Out of 153 DNA samples screened, eight were positive for this product.

The positive clones were analyzed by Southern blot. Briefly, the genomic DNAs were isolated from PCR positive and negative ES clones by phenol/chloroform extraction method. Ten microgram of EcoR I digested genomic DNA from each clone was separated on a 0.8% agarose gel in TAE buffer. The gel was immersed in 0.25% HCl for 10 min, then denatured by soaking in 1 M NaCL/0.5 M NaOH for 30 min and neutralized by soaking in 0.5 M Tris-HCl/NaCl for 30 min. The DNAs were transferred to Nylon membrane (Osmonics, Westborough, Mass.) and hybridized according to the manufacture's instruction at 65° C. for 14 hr. The 0.9 Kb probe was generated by PCR targeting the exon 1 upstream region between EcoR I and Hind III sites. The primers are CTGCAGTGAACACCCCTCTC, SEQ ID NO. 9 and ACGTCTCCAGGTCCTCAGAG, SEQ ID NO. 10. The probe was labeled with $^{32}$P using DECAprime DNA labeling kit (Ambion, Austin Tex.). After hybridization, the blot was washed twice in 1×SSC/0.1% SDS at room temperature for 15 min, followed by two washes in 1%×SSC/0.5% SDS at 65° C. for 15 min.

The blot was exposed to BIOMAX MS film (Kodak, Rochester N.Y.) with a Kodak HE intensifying screen for 2 days at −70° C. A 4.7 Kb fragment and a 7.0 Kb fragment were identified in the PCR positive DNA samples. The 4.7 Kb fragment indicates the endogenous allele present in negative clones. The 7 Kb fragment revealed homologous recombination. Namely, the replacement of 0.9 Kb murine exon2 with 3.2 Kb human exons 2 and 3.

B. Generation of ES Cells with a Functional Humanized CTLA4 Locus by Cre-mediated Excision of the Neo-TK Cassette In a "in vitro" experiment, we excised the neomycin resistance (Neo) and thymidine kinase (TK) genes, flanked by loxP sites, from the humanized CTLA4 transgene in ES cell line #63. We used the pCre-Pac plasmid described by Taniguchi M., et al. 1998 (Nucl Acid Res 26, 679-680, 1998). This plasmid expresses both the Cre-recombinase and puromycin resistance gene, which allows for very fast selection of cells that contain the plasmid. The Cre-recombinase is an enzyme that recombines specific DNA sequences called loxP. A gene that is situated between two loxP sites of the same orientation is effectively excised by the action of the Cre-recombinase.

We transfected the pCre-Pac plasmid into approximately 5 million ES cells of clone #63 by electroporation. After two days of selection with 1 μg/ml puromycin in the growth media, the majority of cells died. The cells that survived expressed transiently both the puromycin resistance gene and the Cre-recombinase. We then continued the selection with Gangcyclovir, a drug that is converted by TK into a toxic metabolite. ES cells that, after Cre-mediated excision, lost the tk gene were not affected by the Gancyclovir and grew into colonies. Twenty colonies were individually isolated and tested for the presence of neo and tk genes. In several such colonies the loss of Neo and TK genes from the humanized CTLA4 mouse transgene was confirmed and the cells were further analyzed.

Figure 5:
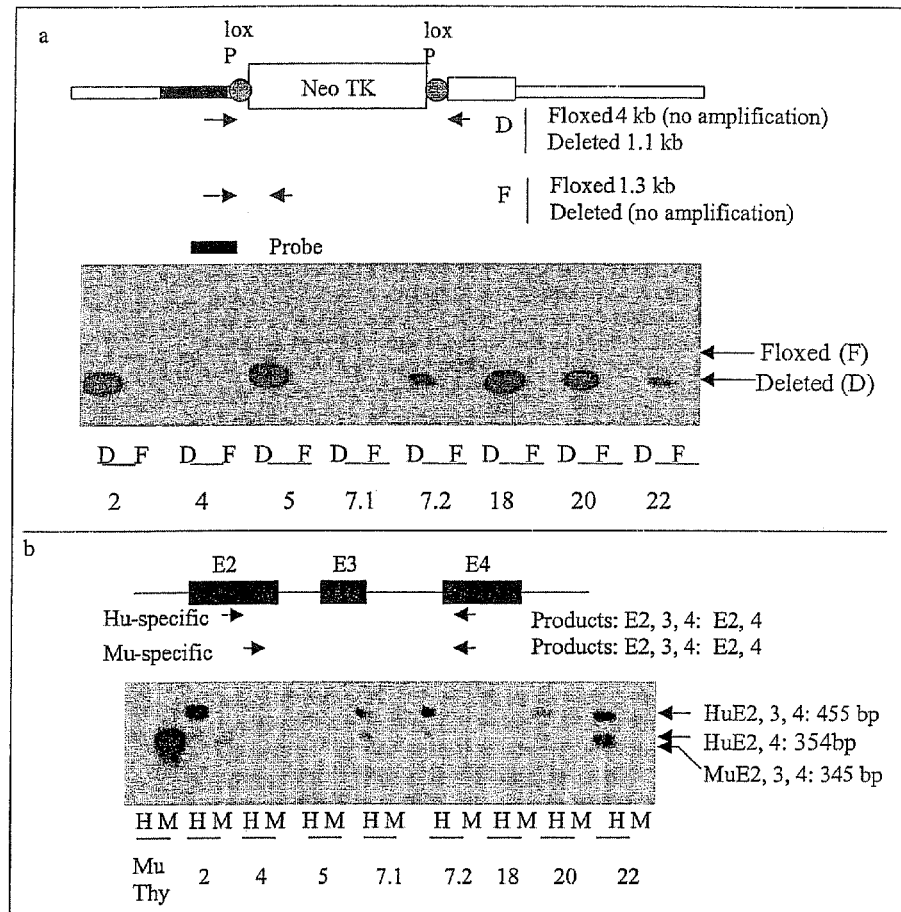
FIG. 5. ES cells with uninterrupted humanized CTLA4 gene locus after removal of the Neo-TK. cassette by transfection with cre recomibinase gene.
  a. Verification of the genomic structure by PCR. The diagram in the first panel shows the positions of the primers used in reaction D and F, which are designed to amplify deleted or floxed locus, respectively. Note that the majority of the clones have deleted locus, although clone 7.2 appears to have some cells with floxed locus.
  b. ES cells with the uninterrupted humanized CTLA4 locus express human CTLA4 mRNA, as revealed by RT-PCR. The diagrams illustrates the position of the primers used to amplify the endogenous murine CTLA4 alleles or the humanized CTLA4 alleles. The majority of the clones express two alternatively spliced form of human CTLA4 genes, and except for clone 2, the expression of the endogenous murine locus was not detected.

As shown in FIG. 5a, two set of PCR reactions were carried out to detect the floxed and deleted alleles of the CTLA4 locus. The first PCR reaction (D) used 5'-TCCCTCTCAGA-CACCTCTGC-3', SEQ ID NO. 11 as the forward primer, and 5'-GTCATAAACATCTCTCAGGTAA-3', SEQ ID NO. 12 as the reverse primer. This reaction amplifies the deleted alleles with a product of 1.1 kb. While this reaction should theoretically also amplify the endogenous murine CTLA4 alleles, the PCR condition used did not allow amplification of a large product of 4 kb (data not shown). As shown in FIG. 5a, clones 2, 5, 7.1, 7.2, 18, 20, 22 have a deleted alleles.

The second PCR (F) used 5'-TCCCTCTCAGACAC-CTCTGC-3', SEQ ID NO. 13 as the forward primer and the 5'-CGACCTGTCCGGTGC-3', SEQ ID NO. 14 as the reverse primer. This PCR only amplified the floxed (TK-Neo containing) alleles. The data shown in FIG. 5a indicated that only clone 7.2 has significant amount of cells with floxed alleles.

C. Expression of the Humanized CTLA4 Gene in ES Cells

It has been reported that ES cells can express CTLA4 gene at low levels (Ling et al., Exp Cell Res 241: 55-65, 1998). To analyze the expression of the humanized CTLA4 alleles in the ES cells with an uninterrupted humanized CTLA4 gene, we designed two sets of RT-PCR reactions to evaluate the expression of the endogenous murine CTLA4 allele as well as those of the humanized alleles. Reaction H used 5'-GAG-GCATCGCCAGCTTTGTG-3', SEQ ID NO. 15 as forward primer, and 5'-CACATAGACCCCTGTTGTAAGA-3', SEQ ID NO.16 as the reverse primer. This reaction did not amplify murine CTLA4 as cDNA prepared from mouse thymus did not yield any product. In the majority of the clones tested (clones 2, 7.1, 7.2, 20 and 22), this reaction detected two forms of humanized CTLA4 gene products: one comprised exons 2 and 3 of the human CTLA4 gene and exon 4 of the murine CTLA4 gene, and the other comprised exon 2 of the human CTLA4 gene and exon 4 of the murine CTLA4 gene (FIG. 5b).

Reaction M used the same reverse primer, but the oligonucleotide corresponding to a unique sequence on murine exon 2, 5'-TGTGCCACGACATTCACAGA-3', SEQ ID NO. 17 as the forward primer. This reaction amplified murine CTLA4. Interestingly, except clone 2, none of the other ES cell clone appeared to express significant amount of murine CTLA4 gene, perhaps due to a lower efficacy of PCR amplification.

Based on the analysis of DNA and RNA, we decide to use clone 2, and clone 22 for the production of transgenic mice.

D. Production of Chimeric and Transgenic Mice

We have chosen clones 63 and 212 for aggregation with embryos of the ICR mice, and transplanted the aggregated embryos into pseudopregnant female mice. The resulting chimera mice are bred to BALB/c mice to obtain germ-line transmission of the targeted CTLA4 alleles. Mice with the targeted alleles, as identified by polymerase chain reaction, are bred to mice with cre-transgene to delete the lox-P flanked Neomycin-resistance (Neo) and thymidine kinase (TK) genes.

Chimeric mice were prepared by an aggregation method essentially as described (Gene Targeting A Practical Approach, Ed. A. L. Joyner, Oxford University Press Inc. New York, 1993). Morula stage embryos of ICR mouse strain are aggregated and cocultured for 24 hrs with 8-16 cells of the ES clones. After 24 hrs the embryos develop to the blastocyst stage and are transplanted to the uteruses of pseudopregnant female mice. After 3 weeks of pregnancy chimeric pups are born and identified by chimerism of the skin which resulted in areas of white and brown fur. The ICR mouse strain is white (albino) and the 129 mouse strain from which the ES cells were derived is brown (agouti). When the ES genotype is passed to the progeny it can be readily identified by the brown coat color. 50% of such animals carry the humanized CTLA4 transgene and can be positively identified by PCR detecting e.g. the human exons, or the neo gene.

Figure 6:
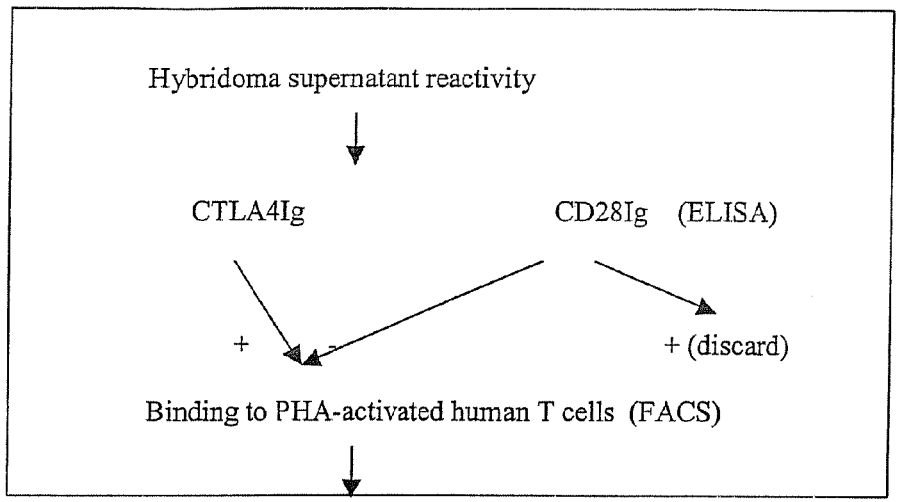
FIG. 6. Diagram of the scheme used for the production and screening of anti-human CTLA4 mAb.

The ES cells that have the homologous recombination can be used directly to produce chimera mice. Alternatively, the ES cells can be transfected with a plasmid that can express Cre gene in the ES cells. Cre protein induces a re-arrangement to delete the lox P flanked Neo-TK casette. As an alternative strategy, we transfected ES cell clone 63 with plasmid pCre-Pac described by Taniguchi M et al (Nucl Acid Res 1998, 26:679-680). The transient transfectants were selected by purimycin for two days. PCR analysis of DNA by PCR and RNA by RT-PCR indicated that the Neo-TK cassette was excised from the knock-in locus, and that the locus is functional in expressing a humanized CTLA4 transgene (FIG. 6).

The chimera mice are bred with BALB/c mice, and the F1 mice that have the coat-color of the 129 mice (agouti) are tested for the presence of the recombined CTLA4 allele. The Neo-TK cassette, if present, is removed by breeding the mice to transgenic mice that express cre gene under the control of the CMV promoter (Jackson laboratories, Me.). The F1 mice are screened for the lack of Neomycin-resistance gene by PCR using 5'CGACCTGTCCGGTGC, SEQ ID NO:14 as forward primer, and 5' CGCCAAGCTCTTCAGC, SEQ ID NO:19, as the reverse primer. Further breeding is carried out to produce mice that are either heterozygous or homozygous for the humanized CTLA4 (CTLA4-H) alleles.

E. Analysis of Human and Murine CTLA4 Expression in the Transgenic Mice

Since the expression of the humanized CTLA4 transgene is under the control of murine CTLA4 regulatory sequence, we expect the expression of the endogenous murine CTLA4A and the humanized CTLA4 transgene to be identical. This is confirmed by two-color flow cytometry for both intracellular and cell-surface CTLA4. Briefly, spleen cells from the heterozygous mice, consisting of one copy of WT murine CTLA4 gene and a copy of the humanized CTLA4 transgene, are activated with Con A for 72 hours. The blast cells are stained with Cytochrome-conjugated anti-human CTLA4 mAb, and PE-labeled anti-mouse CTLA4 (purchased from PharminGen). If expression of the humanized CTLA4 transgene is regulated in the same way as that of murine CTLA4 gene, as expected, we should observe similar expression kinetics in human and murine CTLA4 genes.

Example 3

Production of Anti-Human CTLA4 mAbs

Figure 7:
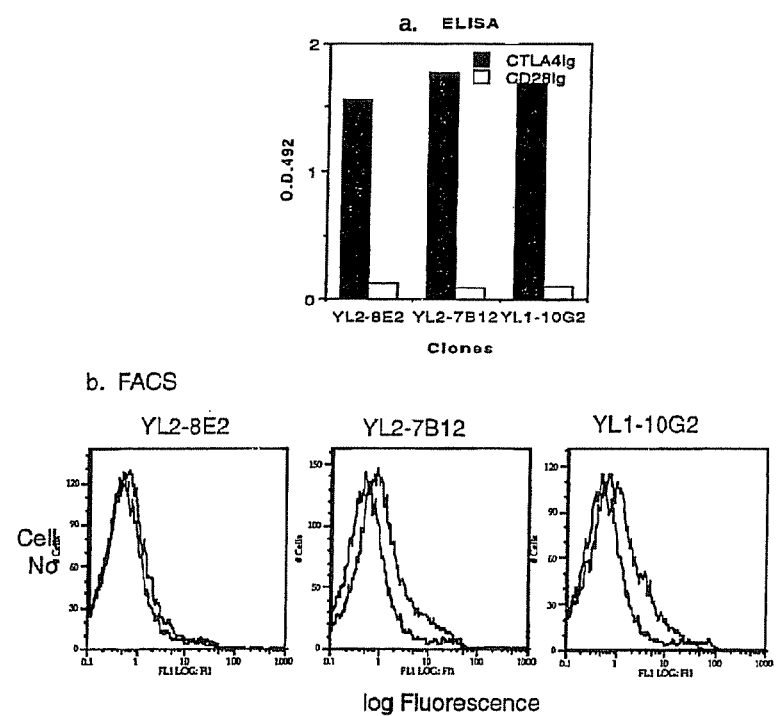
FIG. 7. Production of anti-human CTLA4 mAbs. BALB/c mice were immunized with human CTLA4Ig, and the spleen cells were fused with myeloma. The hybridoma were screened for their binding to human CTLA4Ig but not to CD28Ig. After three consecutive clonings, the supernatants were tested by ELISA (a), and flow cytometry (b) using PHA-activated human PBL. The outer lines in FIG. 6b represent the profile of PHA-activated PBL from the investigator after staining with the given supernatants, while the inner lines are those stained with an irrelevant mAb as control.

We immunized BALB/c mice with fusion protein consisting of the extracellular domain of human CTLA4 protein and the Fc fragment of human IgG1. After two immunizations, the spleen cells were harvested and fused with myeloma cell line XAg8.653. Supernatants were screened according to the diagram in FIG. 6. As shown in FIG. 7, three mAbs bound to CTLA4Ig, but not to CD28Ig in ELISA. In addition, when the mAbs were screened for their binding to activated human PBL, two of the three mAbs showed strong binding while one of them had weak binding.

Example 4

Utilization of Mice with Humanized CTLA4 Gene to Screen for Antibodies with Therapeutic Potential for Human Cancer To test the ability of the anti-human CTLA4 mAb to induce tumor rejection, human CTLA4-H(+/+) mice are challenged with the tumor cell lines known to be susceptible to anti-murine CTLA4-induced immunity. Rejection of wild-type J558 tumor requires CD8. Therefore use this model can be used to screen the ability of anti-human CTLA4 mAbs to induce tumor rejection by enhancing CTL function. Briefly, $5 \times 10^5$ of J558 tumor cells are injected subcutaneously in the flank of the CTLA4-H(+/+) BALB/c mice on day 0. On day 0, 2, 4 after tumor injection, mice are also injected with either isotype-matched murine mAbs or anti-human CTLA4 mAb. Both tumor incidences and tumor size are monitored by physical examination. The mAbs that have an effect on tumor rejection are compared in detail with regard to doses, and time of injection required for the induction of tumor rejection.

The same approach is used to screen for anti-human CTLA4 mAb that can activate NK-mediated tumor rejection. The procedure is identical to what has been described for the J558 tumor, except that a variant of the tumor cells, REB7, which lacks MHC class I and cannot be rejected by CTL, are used. If an antibody induces rejection of J588, but not REB7, it is expected to be valuable for the treatment of cancer in which CTL was the major effector. Typically, this category of cancers includes the majority of cancer cells that retain cell surface of HLA-A, B and C, for example, most of the leukemia, melanoma, breast cancer, prostate cancer, sarcomas, colon cancer, lung cancer, and hepatocellular carcinoma. On the other hand, if the anti-CTLA4 mAbs are more efficient in inducing rejection of REB7, it is expected be more valuable in treating cancer that are more susceptible to NK cell lysis. This category of cancer include those that have lost cell surface HLA-A, B & C expression, such as late stage prostate cancer, small cell lung carcinoma, metastatic cancer of breast, colon, liver, and melanoma origin, and brain tumors.

Example 5

Utilization of the CTLA4-H(+/+) Mice to Screen for Anti-CTLA4-H mAbs that Enhance CTL Recognition of Viral Infected Cells In the mouse model, it is established that anti-CTLA4 mAb can augment CD8 T cell mediated immunity. The CTLA4-H (+/+) mice are used to screen for mAbs that increase the efficacy of host CTL in the clearance of cells infected by intracellular parasites. The CTLA4-H alleles are bred into the F5 transgenic mice with T cell receptor specific for influenza viral peptide NP36-374. Another strain of influenza virus A/PR8 has a single amino acid replacement at position 372, from D to E. The A/PR peptide is recognized at a 10,000 fold lower efficacy. As a result, the F5 T cells can clear infection by A/JAP virus, but not by A/PR8 virus. Since the intranasal A/PR8 virus infection is lethal in mice without prior immunization, the B6 mice are injected with 100 HAU (hemoagglutination units) of A/PR virus intranasally. At the same time, $5\times10^6$ spleen cells are adoptively transferred from the F5-transgenic mice. Half of those mice that received adoptive cell transfer will receive anti-CTLA4-H mAb, while the other half receives an isotype-matched mAb of unrelated specificity. Previous work has established that unmanipulated spleen cells do not convey protection. If anti-CTLA4-H mAb can substantially enhance the activation function of CTL, one may observe protection of the recipient mice against A/PR8 infection, as revealed by increased survival and reduced viral titer in the lung, as measured by the established art.

The mAb that can increase the efficacy of CD8 T cells in combating a virus that otherwise cannot be recognized is of great value in the therapy of chronic infection, such as human immune deficiency virus. It is established that a major mechanism by which HIV evades CTL recognition is by changing the antigenic epitope so as the to render the existing CTL useless. If the anti-CTLA4 mAb can increase the sensitivity of the CTL, one may be able to activate the pre-existing CTL to eliminate the viral variants.

Example 6

Utilization of Mice with Human CTLA4 to Screen for mAbs that May Suppress Autoimmune Diseases The CTLA4-H(+/+) mice can also be used to screen for anti-CTLA4-H mAbs that inhibit autoimmune diseases. Experimental autoimmune encephalomyelitis is used as the first test to screen for anti-CTLA4 mAb that may inhibit autoimmune disease, because of its simplicity and clear-cut clinical outcome.

MOG peptide 35-55 of rat origin (MEVGWYRSPFSRVVHLYRNGK, SEQ ID NO. 18), synthesized by Research Genetics, Inc. (Huntsville, Ala., USA), is used as the immunogen. CTLA4-H(+/+) C57BL/6 mice of 8-12 wks of age are immunized subcutaneously with 200 μg MOG peptide in complete Freund's Adjuvant (400 μg of *Mycobacterium tuberculosis* per ml) in a total volume of 100 μl. Anti-human CTLA4 mAbs or their isotype-matched controls, are administrated on day 0, and +2 of MOG immunization. Animals receive 200 ng of Pertusis toxin (List Biological, Campbell, Calif.) in 200 μl PBS in the tail vein immediately after the immunization, and again 48 hours later. The mice are observed every other day and scored on a scale of 0-5 with gradations of 0.5 for intermediate scores: 0, no clinical signs; 1, loss of tail tone; 2, wobbly gait; 3, hind limb paralysis; 4, hind and fore limb paralysis; 5, death Mice are sacrificed by $CO_2$ inhalation. Spinal cords are removed by insuffocation and fixed in 10% formalin/PBS. Paraffin sections are prepared and stained with hematoxylin and eosin. Neurological lesions are graded on each of the 10 cross sections per spinal cord, according the following criteria; 0, no infiltrate; 1, 3 or less focal meningeal infiltrates; 2, more than 3 focal meningeal infiltrates; 3, up to 5 perivascular infiltrate foci in the parenchyma with involvement of less than 5% of the white matter; 4, 5-10 perivascular foci in the parenchyma or invasions involving 5-25% the white matter; 5, more than 10 perivascular foci or diffuse infiltration involving more than 25% of the white matter.

For the mAbs that show clinical benefit in this model, the test is extended to a model with a longer disease course, namely the myelin-basic protein-induced EAE in the PL/J mice. The PL/J mice develop relapsing experimental autoimmune encephalomyelitis, which is highly reminiscent of human multiple sclerosis. Briefly, the humanized CTLA4 loci is backcrossed into the PL/J mice. After 5 generation of backcross, EAE is induced by MBP according to a established procedure. Half of the MBP-immunized mice also receive anti-CTLA4 mAb at 200 μg/injection/mouse. The mAbs are injected either before, at, or after the clinical onset of disease to determine whether the mAbs prevent the induction, reduce severity of the onset, augment remission, and prevent relapse.

With some modifications, the CTLA4-H(+/+) mice can be used to screen for mAb that inhibit other autoimmune diseases. To screen for anti-human CTLA4 mAb that may suppress autoimmune diabetes, we will breed the humanized CTLA4 gene into the NOD mice that develop spontaneous diabetes within 20 weeks of age. The anti-human CTLA4 mAb are injected at different times after birth to test the time window at which the anti-CTLA4 mAb may interfere with the disease development. The anti-CTLA4 mAb can are also tested in mice that have already developed the disease.

ADDITIONAL REFERENCES

Barbesino, G., Tomer, Y., Concepcion, E., Davies, T. F., and Greenberg, D. A. (1998). Linkage analysis of candidate genes in autoimmune thyroid disease: 1. Selected immunoregulatory genes. International Consortium for the Genetics of Autoimmune Thyroid Disease. J Clin Endocrinol Metab 83, 1580-4.

Braun, J., Donner, H., Siegmund, T., Walfish, P. G., Usadel, K. H., and Badenhoop, K. (1998). CTLA-4 promoter variants in patients with Graves' disease and Hashimoto's thyroiditis. Tissue Antigens 51, 563-6.

Dariavach, P., Mattei, M. G., Golstein, P., and Lefranc, M. P. (1988). Human Ig superfamily CTLA-4 gene: chromosomal localization and identity of protein sequence between murine and human CTLA-4 cytoplasmic domains. Eur J Immunol 18, 1901-5.

Donner, H., Braun, J., Seidl, C., Rau, H., Finke, R., Ventz, M., Walfish, P. G., Usadel, K. H., and Badenhoop, K. (1997). Codon 17 polymorphism of the cytotoxic T lymphocyte antigen 4 gene in Hashimoto's thyroiditis and Addison's disease. J Clin Endocrinol Metab 82, 4130-2.

Donner, H., Rau, H., Walfish, P. G., Braun, J., Siegmund, T., Finke, R., Herwig, J., Usadel, K. H., and Badenhoop, K. (1997). CTLA4 alanine-17 confers genetic susceptibility to Graves' disease and to type 1 diabetes mellitus. J Clin Endocrinol Metab 82, 143-6.

Harper, K., Balzano, C., Rouvier, E., Mattei, M. G., Luciani, M. F., and Golstein, P. (1991). CTLA-4 and CD28 activated lymphocyte molecules are closely related in both mouse and human as to sequence, message expression, gene structure, and chromosomal location. J Immunol 147, 1037-44.

Huang, D., Giscombe, R., Zhou, Y., Pirskanen, R., and Lefvert, A. K. (2000). Dinucleotide repeat expansion in the CTLA-4 gene leads to T cell hyper-reactivity via the CD28 pathway in myasthenia gravis [In Process Citation]. J Neuroimmunol 105, 69-77.

Huang, D., Liu, L., Noren, K., Xia, S. Q., Trifunovic, J., Pirskanen, R., and Lefvert, A. K. (1998). Genetic association of Ctla-4 to myasthenia gravis with thymoma. J Neuroimmunol 88, 192-8.

Jenkins, M. K., Taylor, P. S., Norton, S. D., and Urdahl, K. B. (1991). CD28 delivers a costimulatory signal involved in antigen-specific IL-2 production by human T cells. J Immunol 147, 2461-6.

Karandikar, N. J., Vanderlugt, C. L., Walunas, T. L., Miller, S. D., and Bluestone, J. A. (1996). CTLA-4: a negative regulator of autoimmune disease. J Exp Med 184, 783-8.

Kotsa, K., Watson, P. F., and Weetman, A. P. (1997). A CTLA-4 gene polymorphism is associated with both Graves disease and autoimmune hypothyroidism. Clin Endocrinol (Oxf) 46, 551-4.

Krunmel, M. F., and Allison, J. P. (1995). CD28 and CTLA-4 have opposing effects on the response of T cells to stimulation [see comments]. J Exp Med 182, 459-65.

Leach, D. R., Krummel, M. F., and Allison, J. P. (1996). Enhancement of antitumor immunity by CTLA-4 blockade [see comments]. Science 271, 1734-6.

Linsley, P. S., Brady, W., Umes, M., Grosmaire, L. S., Damle, N. K., and Ledbetter, J. A. (1991). CTLA-4 is a second receptor for the B cell activation antigen B7. J Exp Med 174, 561-9.

Linsley, P. S., Clark, E. A., and Ledbetter, J. A. (1990). T-cell antigen CD28 mediates adhesion with B cells by interacting with activation antigen B7/BB-1. Proc Natl Acad Sci USA 87, 5031-5.

Luhder, F., Hoglund, P., Allison, J. P., Benoist, C., and Mathis, D. (1998). Cytotoxic T lymphocyte-associated antigen 4 (CTLA-4) regulates the unfolding of autoimmune diabetes. J Exp Med 187, 427-32.

Marron, M. P., Raffel, L. J., Garchon, H. J., Jacob, C. O., Serrano-Rios, M., Martinez Larrad, M. T., Teng, W. P., Park, Y., Zhang, Z. X., Goldstein, D. R., Tao, Y. W., Beaurain, G., Bach, J. F., Huang, H. S., Luo, D. F., Zeidler, A., Rotter, J. I., Yang, M. C., Modilevsky, T., Maclaren, N. K., and She, J. X. (1997). Insulin-dependent diabetes mellitus (IDDM) is associated with CTLA4 polymorphisms in multiple ethnic groups. Hum Mol Genet 6, 1275-82.

Moskophidis, D., and Kioussis, D. (1998). Contribution of virus-specific CD8+cytotoxic T cells to virus clearance or pathologic manifestations of influenza virus infection in a T cell receptor transgenic mouse model. J Exp Med 188, 223-32.

Nistico, L., Buzzetti, R., Pritchard, L. E., Van der Auwera, B., Giovannini, C., Bosi, E., Larrad, M. T., Rios, M. S., Chow, C. C., Cockram, C. S., Jacobs, K., Mijovic, C., Bain, S. C., Barnett, A. H., Vandewalle, C. L., Schuit, F., Gorus, F. K., Tosi, R., Pozzilli, P., and Todd, J. A. (1996). The CTLA-4 gene region of chromosome 2q33 is linked to, and associated with, type 1 diabetes. Belgian Diabetes Registry. Hum Mol Genet 5, 1075-80.

Tomer, Y., Barbesino, G., Keddache, M., Greenberg, D. A., and Davies, T. F. (1997). Mapping of a major susceptibility locus for Graves' disease (GD-1) to chromosome 14q31. J Clin Endocrinol Metab 82, 1645-8.

Walunas, T. L., Lenschow, D. J., Bakker, C. Y., Linsley, P. S., Freeman, G. J., Green, J. M., Thompson, C. B., and Bluestone, J. A. (1994). CTLA-4 can function as a negative regulator of T cell activation. Immunity 1, 405-13.

Wu, Y., Guo, Y., Huang, A., Zheng, P., and Liu, Y. (1997). CTLA-4-B7 interaction is sufficient to costimulate T cell clonal expansion. J Exp Med 185, 1327-35.

Zheng, P., and Liu, Y. (1997). Costimulation by B7 modulates specificity of cytotoxic T lymphocytes: a missing link that explains some bystander T cell activation. J Exp Med 186, 1787-91.

Zheng, P., Wu, Y., Guo, Y., Lee, C., and Liu, Y. (1998). B7-CTLA4 interaction enhances both production of antitumor cytotoxic T lymphocytes and resistance to tumor challenge. Proc Natl Acad Sci USA 95, 6284-9.

We claim:

1. A method for screening candidate therapeutic agents for multiple sclerosis (MS), wherein said candidate therapeutic agents interact with the extracellular domain of the human Cytotoxic T-Lymphocyte Antigen 4 (CTLA4), comprising:

(a) injecting antigens that induce MS-like pathology and clinical symptoms into a transgenic mouse whose genome comprises a nucleic acid encoding a humanized CTLA4 and whose T cells express the humanized CTLA4, wherein the humanized CTLA4 comprises an extracellular domain of a human CTLA4, and said nucleic acid comprises exon 2 of a human CTLA4 receptor gene, and exons 1, 3, and 4 of a mouse or human CTLA4 receptor gene, (b) administering the candidate agent to said mouse, and (c) monitoring the development of MS-like pathology and clinical symptoms in said mouse.

2. The method according to claim 1, wherein the candidate therapeutic agent comprises at least one agent chosen from the group consisting of peptides, small organic molecules, peptidomimetics, and antibodies.

3. The method according to claim 2, wherein the candidate therapeutic agent comprises an antibody.

4. The method according to claim 3, wherein the candidate therapeutic agent comprises a monoclonal antibody.

* * * * *

SEQUENCE LISTING

```
<160> NUMBER OF SEQ ID NOS: 19

<210> SEQ ID NO 1
<211> LENGTH: 223
<212> TYPE: PRT
<213> ORGANISM: Mus musculus

<400> SEQUENCE: 1

Met Ala Cys Leu Gly Leu Arg Arg Tyr Lys Ala Gln Leu Gln Leu Pro
1               5                   10                  15

Ser Arg Thr Trp Pro Phe Val Ala Leu Leu Thr Leu Leu Phe Ile Pro
            20                  25                  30

Val Phe Ser Glu Ala Ile Gln Val Thr Gln Pro Ser Val Val Leu Ala
        35                  40                  45

Ser Ser His Gly Val Ala Ser Phe Pro Cys Glu Tyr Ser Pro Ser His
    50                  55                  60

Asn Thr Asp Glu Val Arg Val Thr Val Leu Arg Gln Thr Asn Asp Gln
65                  70                  75                  80

Met Thr Glu Val Cys Ala Thr Thr Phe Thr Glu Lys Asn Thr Val Gly
                85                  90                  95

Phe Leu Asp Tyr Pro Phe Cys Ser Gly Thr Phe Asn Glu Ser Arg Val
                100                 105                 110
```

```
Asn Leu Thr Ile Gln Gly Leu Arg Ala Val Asp Thr Gly Leu Tyr Leu
            115                 120                 125

Cys Lys Val Glu Leu Met Tyr Pro Pro Tyr Phe Val Gly Met Gly
        130                 135                 140

Asn Gly Thr Gln Ile Tyr Val Ile Asp Pro Glu Pro Cys Pro Asp Ser
145                 150                 155                 160

Asp Phe Leu Leu Trp Ile Leu Val Ala Val Ser Leu Gly Leu Phe Phe
                165                 170                 175

Tyr Ser Phe Leu Val Thr Ala Val Ser Leu Ser Lys Met Leu Lys Lys
                180                 185                 190

Arg Ser Pro Leu Thr Thr Gly Val Tyr Val Lys Met Pro Pro Thr Glu
                195                 200                 205

Pro Glu Cys Glu Lys Gln Phe Gln Pro Tyr Phe Ile Pro Ile Asn
    210                 215                 220

<210> SEQ ID NO 2
<211> LENGTH: 223
<212> TYPE: PRT
<213> ORGANISM: Homo sapiens

<400> SEQUENCE: 2

Met Ala Cys Leu Gly Phe Gln Arg His Lys Ala Gln Leu Asn Leu Ala
1               5                   10                  15

Ala Arg Thr Trp Pro Cys Thr Leu Leu Phe Phe Leu Leu Phe Ile Pro
                20                  25                  30

Val Phe Cys Lys Ala Met His Val Ala Gln Pro Ala Val Val Leu Ala
            35                  40                  45

Ser Ser Arg Gly Ile Ala Ser Phe Val Cys Glu Tyr Ala Ser Pro Gly
    50                  55                  60

Lys Ala Thr Glu Val Arg Val Thr Val Leu Arg Gln Ala Asp Ser Gln
65                  70                  75                  80

Val Thr Glu Val Cys Ala Ala Thr Tyr Met Thr Gly Asn Glu Leu Thr
                85                  90                  95

Phe Leu Asp Asp Ser Ile Cys Thr Gly Thr Ser Ser Gly Asn Gln Val
                100                 105                 110

Asn Leu Thr Ile Gln Gly Leu Arg Ala Met Asp Thr Gly Leu Tyr Ile
            115                 120                 125

Cys Lys Val Glu Leu Met Tyr Pro Pro Pro Tyr Tyr Leu Gly Ile Gly
        130                 135                 140

Asn Gly Thr Gln Ile Tyr Val Ile Asp Pro Glu Pro Cys Pro Asp Ser
145                 150                 155                 160

Asp Phe Leu Leu Trp Ile Leu Ala Ala Val Ser Ser Gly Leu Phe Phe
                165                 170                 175

Tyr Ser Phe Leu Leu Thr Ala Val Ser Leu Ser Lys Met Leu Lys Lys
                180                 185                 190

Arg Ser Pro Leu Thr Thr Gly Val Tyr Val Lys Met Pro Pro Thr Glu
                195                 200                 205

Pro Glu Cys Glu Lys Gln Phe Gln Pro Tyr Phe Ile Pro Ile Asn
    210                 215                 220

<210> SEQ ID NO 3
<211> LENGTH: 24
<212> TYPE: DNA
<213> ORGANISM: Mus musculus

<400> SEQUENCE: 3
```

```
ctgaagcttc agtttcaagt tgag                                              24

<210> SEQ ID NO 4
<211> LENGTH: 20
<212> TYPE: DNA
<213> ORGANISM: Mus musculus

<400> SEQUENCE: 4
ttggatggtg aggttcactc                                                   20

<210> SEQ ID NO 5
<211> LENGTH: 30
<212> TYPE: DNA
<213> ORGANISM: Mus musculus

<400> SEQUENCE: 5
atcctctaga agcttcaaag caggttatca                                        30

<210> SEQ ID NO 6
<211> LENGTH: 30
<212> TYPE: DNA
<213> ORGANISM: Mus musculus

<400> SEQUENCE: 6
tctagtcgac cacagagagt caaggccctg                                        30

<210> SEQ ID NO 7
<211> LENGTH: 20
<212> TYPE: DNA
<213> ORGANISM: Mus musculus

<400> SEQUENCE: 7
ccaagactcc acgtctccag                                                   20

<210> SEQ ID NO 8
<211> LENGTH: 20
<212> TYPE: DNA
<213> ORGANISM: Homo sapiens

<400> SEQUENCE: 8
cctctgagca tccttagcac                                                   20

<210> SEQ ID NO 9
<211> LENGTH: 20
<212> TYPE: DNA
<213> ORGANISM: Mus musculus

<400> SEQUENCE: 9
ctgcagtgaa caccctctc                                                    20

<210> SEQ ID NO 10
<211> LENGTH: 20
<212> TYPE: DNA
<213> ORGANISM: Mus musculus

<400> SEQUENCE: 10
acgtctccag gtcctcagag                                                   20

<210> SEQ ID NO 11
<211> LENGTH: 20
<212> TYPE: DNA
<213> ORGANISM: Mus musculus
```

-continued

```
<400> SEQUENCE: 11
tccctctcag acacctctgc                                                    20

<210> SEQ ID NO 12
<211> LENGTH: 22
<212> TYPE: DNA
<213> ORGANISM: Mus musculus

<400> SEQUENCE: 12
gtcataaaca tctctcaggt aa                                                 22

<210> SEQ ID NO 13
<211> LENGTH: 20
<212> TYPE: DNA
<213> ORGANISM: Mus musculus

<400> SEQUENCE: 13
tccctctcag acacctctgc                                                    20

<210> SEQ ID NO 14
<211> LENGTH: 15
<212> TYPE: DNA
<213> ORGANISM: Artificial Sequence
<220> FEATURE:
<223> OTHER INFORMATION: PCR primer hybridizing to Neo TK sequences.
<220> FEATURE:
<221> NAME/KEY: misc_feature
<222> LOCATION: (1)..(15)
<223> OTHER INFORMATION: PCR Primer from TK-Neo Gene

<400> SEQUENCE: 14
cgacctgtcc ggtgc                                                         15

<210> SEQ ID NO 15
<211> LENGTH: 20
<212> TYPE: DNA
<213> ORGANISM: Homo sapiens

<400> SEQUENCE: 15
gaggcatcgc cagctttgtg                                                    20

<210> SEQ ID NO 16
<211> LENGTH: 22
<212> TYPE: DNA
<213> ORGANISM: Mus musculus

<400> SEQUENCE: 16
cacatagacc cctgttgtaa ga                                                 22

<210> SEQ ID NO 17
<211> LENGTH: 20
<212> TYPE: DNA
<213> ORGANISM: Mus musculus

<400> SEQUENCE: 17
tgtgccacga cattcacaga                                                    20

<210> SEQ ID NO 18
<211> LENGTH: 20
<212> TYPE: PRT
<213> ORGANISM: Rattus sp.

<400> SEQUENCE: 18

Met Glu Val Gly Trp Tyr Arg Ser Pro Phe Ser Arg Val Val His Leu
```

-continued

```
        1               5              10              15
Arg Asn Gly Lys
            20

<210> SEQ ID NO 19
<211> LENGTH: 16
<212> TYPE: DNA
<213> ORGANISM: Artificial Sequence
<220> FEATURE:
<223> OTHER INFORMATION: PCR primer

<400> SEQUENCE: 19
cgccaagctc ttcagc                                                    16
```